United States Patent [19]

Fischer

[11] Patent Number: 5,679,378
[45] Date of Patent: Oct. 21, 1997

[54] METHOD AND MATERIAL FOR HAIR THERAPY

[75] Inventor: Raymond Robert Fischer, Tiberias, Israel

[73] Assignee: Olim Industries of Israel, North America, Ltd., Lafayette, Calif.

[21] Appl. No.: 746,932

[22] Filed: Nov. 18, 1996

Related U.S. Application Data

[60] Provisional application No. 60/008,813, Dec. 18, 1995.

[51] Int. Cl.$^6$ .............. A61K 33/00; A61K 33/34; A61K 33/32; A61K 33/26
[52] U.S. Cl. .............. 424/600; 424/630; 424/639; 424/641; 424/646; 424/652; 424/654; 424/655; 424/657; 424/661; 424/682; 424/709; 424/724; 514/880
[58] Field of Search .............. 424/600, 630, 424/639, 641, 646, 652, 654, 655, 657, 661, 682, 709, 724; 514/880

[56] References Cited

U.S. PATENT DOCUMENTS

| | | | |
|---|---|---|---|
| 4,139,619 | 2/1979 | Chidsey, III | 424/45 |
| 4,596,812 | 6/1986 | Chidsey, III et al. | 514/256 |
| 5,157,036 | 10/1992 | Grollier | 514/256 |
| 5,177,061 | 1/1993 | Pickart | 514/18 |
| 5,178,883 | 1/1993 | Knighton | 424/532 |
| 5,183,817 | 2/1993 | Bazzano | 514/256 |
| 5,373,006 | 12/1994 | Grollier | 514/275 |
| 5,401,503 | 3/1995 | Murayama | 424/195.1 |
| 5,407,944 | 4/1995 | Goldman | 514/310 |
| 5,443,823 | 8/1995 | Rosenbaum et al. | 424/70.1 |
| 5,466,694 | 11/1995 | Terranova et al. | 514/272 |
| 5,466,695 | 11/1995 | Poulos et al. | 514/275 |
| 5,470,861 | 11/1995 | Harmon | 514/337 |
| 5,470,876 | 11/1995 | Proctor | 514/492 |
| 5,480,889 | 1/1996 | Goldman | 514/310 |
| 5,498,603 | 3/1996 | Clodman et al. | 514/25 |
| 5,514,672 | 5/1996 | Bazzano | 514/168 |
| 5,538,945 | 7/1996 | Pallenberg et al. | 514/6 |
| 5,547,957 | 8/1996 | Gormley et al. | 514/284 |

OTHER PUBLICATIONS

*Awakening, Authentic Black Mud Body and Hair Treatment* (product packaging which includes Black Mud ingredients). (Jul. 1994).
BIOSIS 92:387315, Sukenik et al. 1992.

*Primary Examiner*—Kimberly Jordan
*Attorney, Agent, or Firm*—Coudert Brothers

[57] ABSTRACT

The invention is directed to Dead Sea mud for restoration of hair growth and retardation of hair loss for those suffering from alopecia and a hair therapy method of topically applying to the scalp of a human or other mammal scalp an effective amount of the Dead Sea mud. Dramatic results in overall hair therapy have been obtained by those individuals that have practiced the present method for a relatively short period of time.

19 Claims, No Drawings

METHOD AND MATERIAL FOR HAIR THERAPY

This application claims the benefit of prior U.S. provisional application Ser. No. 60/008,813, filed Dec. 18, 1995.

FIELD OF THE INVENTION

This invention relates generally to the restoration of hair growth over certain surface areas of the body (sometimes called "bald areas" herein) on which hair growth has ceased or diminished. More particularly, the invention relates to a method and a material for the restoration of hair growth and for the retardation of hair loss.

BACKGROUND OF THE INVENTION

Androgenic alopecia is the most common form of hair loss in both men and women. Hair loss affects approximately one third of those with a strong family history of baldness. It is a genetic disorder transmitted as an autosomal dominant gene. Therefore, the gene can come from either the paternal or maternal side of the family and effect men and women. The patterns of hair loss are different in men and women, but the mechanisms appear the same. Through successive development of some individuals carrying such a gene, the hair follicles get smaller and the hair itself gets finer. In many cases the final result is total baldness, especially in the crown. In other individuals, there is generalized thinning or temporal recession of the hair line. The active process may start in the teens and continue through the 40's and may not stabilize even in the 50's.

Although the only accepted physical effect of hair loss is cosmetic (even though there is some evidence that men with androgenic alopecia have an increased risk of cardiovascular disease), the psychological effects can be devastating. The pressure to find an effective treatment is immense.

Methods and materials for bringing about the restoration of hair growth on surface areas of the human body over which natural, unaided hair growth has ceased or diminished are well known in the prior art. A representative listing of the more recent prior art on this subject include: U.S. Pat. Nos. 5,157,036; 5,177,061; 5,178,883; 5,183,817; 5,373,006; 5,401,503; 5,407,944; 5,443,823; 5,466,694; 5,466,695; 5,470,861; 5,470,876; 5,480,889; 5,498,603; 5,514,672; 5,538,945; and 5,547,957.

The foregoing partial list attests to the effort and ingenuity, including inventive effort and systematic research, that has been applied to seeking a solution to the problem of restoring hair growth on certain surface areas of the human body over which natural, unaided hair growth has ceased or diminished.

These prior art efforts have included the development and application of certain massage techniques to such bald areas, both by manual manipulation alone and with the aid of certain mechanical devices, or by the sole use of certain mechanical devices. Such prior art attempts to restore the growth of hair over certain surface areas of the human body have also involved the application of heat, electromagnetic radiation, and selected ionizing atmospheres to such surface areas of the human body.

Other prior art methods of human hair growth restoration have involved the application of certain chemical elements, compounds, or mixtures thereof, to such bald areas. Generally, the substances (elements and compounds) or mixtures thereof have been applied topically to such bald areas of the scalp. Minoxidil, an anti-hypertensive compound, is an example of such a man-made substance as discussed in U.S. Pat. Nos. 4,139,619 and 4,596,812. Minoxidil is mixed with other materials and sold in the United States of America under the trademark ROGAINE. While the minoxidil is recognized as being somewhat effective in causing new growth of vellus hairs with some terminal hair growth in a preselected group of subjects, it is not effective in a large number of subjects. Vellus hairs are fine, thin, non-pigmented short hairs in which the bulb of the hair follicle is seated superficially in the dermis of the scalp. Terminal hairs, on the other hand are coarse, pigmented and long and are located deep in the dermis. As alopecia develops, terminal hairs change from terminal to the vellus type in the area approaching baldness.

Presently a great need exists for a composition that is more effective in restoring hair growth and retarding hair loss of individuals suffering from alopecia.

SUMMARY OF THE INVENTION

Accordingly, it is an object of the present invention to provide improved methods and materials for use in bringing about the restoration of hair growth on certain surface areas of the human and other mammalian bodies and the retardation of the loss of hair from such surface areas. Other objects of the present invention will be apparent hereinafter.

In accordance with a principal feature of the present invention, a naturally occurring material, Dead Sea mud, is utilized as a hair therapy material by applying an effective mount of the material to the surface area to be treated. By the phrase "hair therapy", it is intended to mean the treatment of the body where hair is desired, e.g., the scalp, either for the restoration of the growth of hair or for the retardation of hair loss or for both restoration and retardation.

The method of the present invention comprises topically applying a finite layer of Dead Sea mud to the body surface area to be treated for hair therapy, allowing the layer to be undisturbed for a finite period of time, and rinsing the layer from the surface area.

DETAILED DESCRIPTION OF THE PREFERRED EMBODIMENTS

The naturally occurring material applied to completely or partially bald areas of the body in accordance with the method of the present invention is found in certain areas of Israel and Jordan known as the Dead Sea, and is called "Dead Sea mud". The Dead Sea approximately 60 miles in length shares the borders of Israel and Jordan and is famous for its spas and baths. Dead Sea mud consists of more than 100 meters of sediment accumulated from the river Jordan over 15,000 years. Based on extensive medical research, Dead Sea mud has shown remarkable positive effects on rheumatoid arthritis and psoriasis. There have been a number of mechanisms for such effects including that of increased cellular magnesium. The fact remains that such Dead Sea mud (extract) have been found to have significant influences on both the skin and the immune system. However, prior to the present invention, no one has ever proposed applying materials from the Dead Sea on completely or partially bald areas of the human body for a sufficient period of time and noting the effect.

Dead Sea mud has been analyzed by the Ministry of Health and Infrastructure, Geological Division, of the State of Israel; one such analysis having been carried out in March of 1989. As a result of this analysis, Dead Sea mud was determined to be a naturally occurring mixture containing the following elements, in the respective proportions set out hereinbelow.

| NAME OF ELEMENT | PPM |
|---|---|
| Aluminum | 3.5 |
| Boron | 3.0 |
| Barium | 1.1 |
| Beryllium | <0.1 |
| Cadmium | <0.1 |
| Chromium | 0.4 |
| Cobalt | 0.3 |
| Copper | 0.1 |
| Iron | 0.3 |
| Manganese | 5.0 |
| Molybdenum | <0.5 |
| Nickel | <0.3 |
| Lead | <0.5 |
| Silicone | 4.0 |
| Strontium | 46.0 |
| Vanadium | <0.2 |
| Zinc | <0.1 |
| Sodium | 6000.0 |
| Potassium | 2350.0 |
| Calcium | 3450.0 |
| Magnesium | 6000.0 |
| Chloride | 34000.0 |
| Sulphate | 3070.0 |
| Bromide | 800.0 |

It is to be understood that the hair therapy material of the present invention may be modified as compared with naturally occurring, unmodified Dead Sea mud without having any positive or negative affect on hair growth. Thus, certain well known and commercially available scent altering materials, as well as softening, hydrating, moisturizing, anti-bacterial agents, colorants, and other conventional adjunctive compounds may be added to the naturally occurring Dead Sea mud during the production of the hair therapy material of the present invention, which is applied according to the method of the present invention.

The hair growth restoring material of the present invention which was the subject of investigations described in the examples below was, in the container as received by the user, free of standing water. However, it is to be understood that the hair growth restoring material of the present invention may, as supplied by the user, be diluted to a limited degree, preferably with waters obtained from the Dead Sea.

During the manufacture of the hair therapy material of the present invention, the naturally occurring Dead Sea mud is removed from the Dead Sea bed and washed with deionized water to remove substantially all of the gravel and sand. The washed Dead Sea mud is filtered through a vibrating sieve to remove the remaining gravel and sand from the washing step. The Dead Sea mud may be mechanically mixed by stirring or milling to assure homogeneity of apparent color. The montmorillonite structure of the naturally occurring mud appears to cause the mud to settle into strata if left untouched. Therefore, upon standing for periods of time, the unmodified Dead Sea mud settles to the bottom of the container and free standing water is present on the top. This separation can be avoided by the addition of phase stabilizers such as bentonite, a hydrolyzed colloidal aluminum silicate clay.

In performing the method of the present invention, the Dead Sea mud is topically applied with the fingers to the dry scalp and hair, starting at the crown of the head.

An effective amount of the hair therapy material of the present invention is needed in order to produce the optimum restorative effect. The phase "effective amount" is defined herein as the amount of the hair therapy material of the invention necessary to cover all of the skin so that it is completely obscured from view, and to coat any remaining hair, in the targeted treatment area.

After being applied to the treatment area, the hair therapy material of the present invention should be allowed to remain in place for a finite time before being rinsed off the treatment area. The rinsing step is preferably with warm water alone, without soap. The material should remain undisturbed for at least about one minute to about 45 minutes before rinsing. Longer times of application are acceptable, but such longer times of application do not produce any significant results compared with shorter times. Applications of the hair therapy material for up to 120 minutes have not produced any harmful side effects. Before one can expect noticeable results, an effective amount of the hair therapy material should be applied to the treatment area, preferably about 25 to about 40 minutes per day, for at least about 15 days and preferably for at least about 60 days. If the material is applied less frequently, the period of application should be longer before one will see noticeable results.

In accordance with a preferred embodiment of the present invention, the hair therapy material of the present invention is 100% undiluted and unscented black mud of the Dead Sea, that has been washed and filtered to remove gravel and sand. The rich montmorillonite structure of this mud consists of decomposed vegetable matter and the natural soils of the area.

The examples which follow illustrate the superior performance of the hair therapy material of the present invention. The examples are for illustrative purposes only and are not meant to limit the scope of the claims in any way.

EXAMPLES

Example 1

The initial investigation and reduction to practice of the present method was begun by the inventor after a spark of genius led him to begin to apply to his bald scalp 100% undiluted and unscented Dead Sea mud. Since the mud did not contain any phase stabilizers to prevent separation, about a half an ounce of water formed on the top of the container, a 14 ounce wide mouth jar with a screw top lid. He began liberally applying the mud over his entire scalp in a layer deep enough to completely cover the skin and over the little remaining hair of his scalp. He intuitively allowed each application of mud to remain on his scalp for about 30 to 45 minutes. He then showered it off with warm water. After he had faithfully repeated this treatment procedure every other day for an period of six weeks, he and his spouse clearly noticed the growth of new hair where no hair had existed before. Many sprouts of this new hair were evident upon closer inspection. Some of these new sprouts were fully developed terminal hairs and many of the sprouts were growing from new vellus hair at various degrees of maturity. The new growth was most intense and noticeable from each side of mid-scalp and the hair was growing towards the center of the scalp. He has continued the hair therapy method of the present invention for over 22 continuous months. At present his scalp contains approximately 25% regrowth over the entire previously bald scalp. He has totally stopped losing his hair and the hair feels healthier than before using the Dead Sea mud in accordance with the method of this invention.

Example 2

After the initial six week investigation, the inventor confided in a close friend and his brother, each of whom have androgenic alopecia. These two individuals have been practicing the hair therapy method of this invention with similar success.

After such initial success, the inventor was made aware that a more scientific study of this method was advisable. However, the difficulty was recognized in obtaining volunteers to apply the 100% undiluted and unscented Dead Sea mud because of its unappealing natural odor. Consequently, the hair therapy material used in Example 3 below was mixed using an electric powered high shear mixer with bentonite to prevent water separation and a minimal amount of perfume to provide a more pleasing fragrance for the Dead Sea mud and with anti-bacterial and anti-microbial agents. This mechanical mixing step took about 25 minutes. The formulation used in Example 3 is as set forth in Table 1. The PHENOIP additive is manufactured by Nipa Laboratories, Wilmington, Del. The GLYDANT PLUS additive is manufactured by Lonza Company, Fairlawn, N.J.

TABLE 1

| Component | Trade Name | Parts By Weight |
|---|---|---|
| Dead Sea mud plus fragrance | | 100 |
| Phenoxyethanol and methyl, ethyl, propyl and butyl parabans | PHENONIP | 0.4 |
| DMDM hydantoin and iodopropynyl butylcarbamate | GLYDANT PLUS | 0.2 |
| Bentonite | | 2.0 |

Example 3

The results set forth below are based on only five months of an ongoing twelve month study involving a total of 29 male subjects under the supervision of an M.D. to verify the previous successful results obtained from the hair therapy method of the present invention. The successful results obtained after such a short period is unexpected especially when compared with other studies of hair growth restoration products which require much longer periods of time before any positive results are observed. All of the participants in this study had some form of androgenic alopecia and were recruited through flyers in health clubs, barber shops, newspaper advertisements and by word of mouth. All of the participants volunteered for this study and were not paid for their time. They each filled out a standard health questionnaire to determine if there were any complicating medical factors for their apparent hair loss. Only those having good general health between the ages of 18 and 60 that had not used minoxidil in the past four months were accepted. The age of those enrolled in this study ranged from 23 to 59, with a weighted average age of 44.9 years. The extent of baldness of each of the volunteers were determined by physical observation and they were divided into four groups depending upon the pattern and extent of hair loss as set forth in Table 2 below.

Each of the participants was first given verbal instructions on the use of the material of the present invention during an initial individual orientation session. During the orientation, follicle-hair counts were performed by placing a template having a single one centimeter square opening over a representative area on the subject's scalp. The hairs of the representative area within the opening were carefully inspected to determine if they were either terminal or indeterminate based on whether or not they were vellus or non-vellus. Vellus hairs were not counted. The exact representative area was pinpointed by using a coordinate measurement system of distinct anatomical landmarks, e.g. the auricles and the naso-occipital line. An initial photograph was taken of the macro scalp of each participant by a professional photographer using a high quality Rolex® camera system. After the orientation, they were given written instructions and supplied with the hair therapy material at no cost.

The method each participant followed was to place an amount of the hair therapy material in their palm and manually apply a layer of the material over at least a portion of the scalp including the template area. Initially the participants were asked to apply the layer to a thickness of an ordinary sheet of paper. After numerous concerns on the difficulty in making such a measurement, the participants were asked to simply apply the material to a smooth and uniform thickness to completely cover and obscure from view the area to be treated. They allowed the material to remain undisturbed on the scalp for a time ranging from a minimum of five minutes for five days per week to a maximum of 120 minutes for seven days per week. After each application, they showered with clean, warm water free of any cleansing agents to thoroughly rinse the material from their scalps.

Each subject took part in a measurement session on a monthly basis. Two observers independently counted the follicle-hairs and recorded their results. Each subject was asked about the frequency of use, quantity of material used, the exact location on the scalp and the length of time the material was applied, and whether any side effects were experienced. No side effects have been reported to date. A photograph was taken at each measurement session. The subjects were also asked to give their personal evaluation of the results on a scale of 0 (no impact), 1, 2 and 3 (marked impact) as set forth in Tables 3 and 4 below. Finally, they were asked to comment on any changes in the rate of hair loss and to give their observations on the number of hairs left on the shower drain. The data given in the Tables 2, 3 and 4 below are calculated by averaging the findings of the two observers.

The term "slope" is defined herein to mean the rate of hair change in units of "the number of new hairs per month", which is calculated by subtracting the average follicle hair count of the subject at the initial evaluation from the most recent measurement session and dividing by the number of months observed.

The phrase "increase factor" is defined herein to mean the relative increase of follicle hairs over the initial hair count calculated by dividing the follicle-hair count of the latest measurement session by the initial count of a given subject.

The slope and increase factor data of Tables 2, 3 and 4 include only these participants that completed at least three consecutive months of at least infrequent application.

TABLE 2

| Category of Baldness | Description of Baldness | Number of Participants After at Least 3 Months for Slope | Slope Average | Number of Participants After 4 Months for Increase Factor | Increase Factor at 4 Months |
| --- | --- | --- | --- | --- | --- |
| 1 | Totally bald crown. | 7 | 8.4 | 1 | 1.1 |
| 2 | Patchy central area. | 12 | 8.9 | 7 | 3.2 |
| 3 | Thinning hair. | 9 | 10.5 | 4 | 2.5 |
| 4 | Receding hairline. | 1 | 18.5 | 1 | 2.9 |

TABLE 3

| Participant's Observations | Personal Evaluation | Number of Participants After at Least 3 Months for Slope | Slope Average | Number of Participants After 4 Months for Increase Factor | Increase Factor at 4 Months |
| --- | --- | --- | --- | --- | --- |
| 0 | No impact. | 4 | 9.0 | 1 | 3.2 |
| 1 | Minimal impact. | 5 | 7.2 | 0 | — |
| 2 | Moderate impact. | 11 | 10.2 | 9 | 2.1 |
| 3 | Marked impact. | 3 | 11.7 | 3 | 2.1 |

TABLE 4

| Age | Category of Baldness | Description of Baldness | Frequency of Application | Time of Treatment, minutes | Time with the Study, months | Personal Evaluation | Slope | Increase Factor at 4 Months |
| --- | --- | --- | --- | --- | --- | --- | --- | --- |
| 40 | 1 | Totally bald crown. | Daily | 30–60 | 5 | 2 | 2.60 | 1.1 |
| 50 | 2 | Patchy central area. | Daily | 45 | 2 | 2 | 2.50 | |
| 46 | 3 | Thinning hair. | Daily | 60 | 4 | 1 | 9.30 | |
| 57 | 2 | Patchy central area. | Daily | 30 | 5 | 0 | 10.50 | 3.2 |
| 23 | 3 | Thinning hair. | Daily | 60–90 | 3 | 2 | 12.00 | |
| 51 | 2 | Patchy central area. | Infrequent | 30 | 4 | 1 | 5.00 | |
| 45 | 3 | Thinning hair. | Six/week | 20–30 | 3 | 1 | 4.25 | |
| 44 | 3 | Thinning hair. | Daily | 45 | 4 | 2 | 13.00 | 2.5 |
| 41 | 1 | Totally bald crown. | Daily | 40 | 3 | 0 | 8.25 | |
| 44 | 2 | Patchy central area. | Daily | 30 | 4 | 2 | 22.00 | 7.0 |
| 43 | 2 | Patchy central area. | Daily | 30–90 | 2 | 0 | 5.25 | |
| 43 | 3 | Thinning hair. | Daily | 45 | 5 | 3 | 7.25 | 1.7 |
| 47 | 2 | Patchy central area. | Five/week | 5 | 5 | 2 | 2.25 | 1.3 |
| NA | 3 | Thinning hair. | Daily | 60 | 5 | 2 | 11.00 | 2.6 |
| 45 | 2 | Patchy central area. | Daily | 60 | 5 | 2 | 5.75 | 1.7 |
| 32 | 4 | Receding hairline. | Five/week | 15–20 | 5 | 3 | 18.50 | 2.9 |
| 44 | 2 | Patchy central area. | Daily | 30–60 | 5 | 3 | 9.00 | 1.7 |
| 41 | 1 | Totally bald crown. | Daily | NA | 5 | NA | 9.00 | |
| 46 | 2 | Patchy central area. | Daily | 30–45 | 5 | 2 | 10.50 | 2.2 |
| 47 | 1 | Totally bald crown. | Daily | 5 | 3 | 1 | 13.00 | |
| 56 | 3 | Thinning hair. | Daily | 120 | 3 | 0 | | |
| 52 | 2 | Patchy central area. | Daily | 60 | 3 | 1 | 3.20 | |
| 52 | 3 | Thinning hair. | Daily | 30–60 | 4 | 2 | 12 | 2.6 |
| 33 | 2 | Patchy central area. | Five/week | 60 | 5 | 2 | 13 | 3.1 |

Both of the observers recorded significant hair growth in the 23 participants suffering from androgenic alopecia that have continued with the study. They observed a distinct difference between the effects of the hair therapy material of this invention based on the age. The younger subjects had more marked hair growth restoration compared with those that were older and had more advanced hair loss.

Three subjects of a total of 29 participants dropped out of this study. None of the 29 participants reported any problems or side effects from taking the hair therapy material. Two of the subjects that dropped out were not diligent in their application of the material and did not indicate the duration of their application. They showed little if any hair growth restoration. The other subject was not heard from after the initial evaluation, despite repeated mail and telephone inquiries. Therefore, no conclusions at all can be drawn from this subject.

Of the 23 participants that have been in the study for at least three months and who have responded to the latest measurement session, 14 were in the moderate or marked impact group, i.e. groups 2 or 3. Since the group number is subjective based on the observations of the participants, those in the minimal to no impact group require some comment. Part of this group's observations are based on not readily seeing new growth in the crown area recorded by the two third party observers. In addition, these participants reported they had been influenced by friends and family members. There were instances of subjective observations of 0 even though the two third party observers noted very significant growth. This can be explained due to the early extent of the change, the subtle nature of the early changes and the inaccessibility of the new growth of personal view. On the other hand, some of those that rated themselves in groups 2 or 3 had below average slopes and increase factors.

Based on the comments of those rating themselves in this manner, they were pleased with the significant growth outside the 1 square centimeter test area.

The range of the slope data for those that had at least three months of participation in the study was from 2.25 to 22.0, for an average of 9.69. In general, the highest slopes, i.e. over 12, were for those participants who were younger and those with only thinning hair (category 3). The range of the increase factor dam at four months was from 1.1 to 7.0, for an average of 2.5.

The foregoing data were analyzed to determine the effect that duration of the application of the material of this invention has on hair growth restoration. Based on these data, the period can be below 5 minutes per treatment provided the treatments are at least five days per week. Based on experience with hair conditioners and the like, a practical minimum to produce some effect is at least one minute per day. Most of the subjects did allow the material to remain on their scalps for at least 30 minutes before rinsing. No discernable benefit was noted with these participants when the duration of application substantially exceeded 30 minutes.

Based on the common observations of the 23 participants still in the study, the material of this invention not only is effective in hair restoration, but is also effective in retardation of hair loss. Other observations of the participants were their scalps felt better and their hair felt thicker and in generally better condition after using this material for a period of time.

A proposed formula for a commercial form of the hair therapy material of the present invention is set forth in Table 5. In addition to the Dead Sea mud, the phase stabilizing and fragrance agents, and the anti-bacterial and anti-microbial agents of the hair therapy material of Example 3, essential oils and other agents are mechanically mixed into the formulation for their softening, hydrating, moisturizing, reviving, and invigorating effects.

TABLE 5

| Component | Trade Name | Part By Weight |
|---|---|---|
| Dead Sea mud plus fragrance | | ~100 |
| Sodium laureth sulfate | | 4.0 |
| Cocamide DEA | | 0.6 |
| Cocamidopropyl betaine | | 0.5 |
| Jojoba oil | | 0.4 |
| Peach kernel oil | | 0.4 |
| Rosemary oil | | 0.4 |
| Phenoxyethanol and methyl, ethyl, propyl and butyl parabans | PHENONIP | 0.4 |
| DMDM hydantoin and iodopropynyl butylcarbamate | GLYDANT PLUS | 0.2 |
| Bentonite | | 2.0 |

Without departing from the spirit and scope of this invention, one of ordinary skill in the art can make various changes and modifications to the invention to adapt it to various usages and conditions. For example, in the above formulation the 100 parts by weight of Dead Sea mud can be diluted with up to about 50 parts by weight of water and inert filler materials without greatly affecting the benefits of the hair material of the present invention. As such, these changes and modifications are properly, equitably, and intended to be, within the full range of equivalents of the following claims.

What is claimed is:

1. The method for the restoration of hair growth or for the retardation of hair loss which comprises the steps of:

applying a finite layer of Dead Sea mud to the body surface area to be treated for the restoration of hair growth or for the retardation of hair loss;

allowing said layer to be undisturbed for a finite time; and rinsing said layer from said surface area.

2. The method of claim 1 wherein the layer is allowed to remain undisturbed for at least about one to about 45 minutes before rinsing.

3. The method of claim 1 wherein the layer is allowed to remain undisturbed for at least about 25 to about 40 minutes before the rinsing step.

4. The method of claim 1 wherein the steps are repeated for a period of at least about 15 days.

5. The method of claim 1 wherein the steps are repeated for a period of at least about 60 days.

6. The method for the restoration of hair growth or for the retardation of hair loss which comprises the steps of:

applying a layer of Dead Sea mud to the body surface area to be treated having a thickness sufficient to obscure from view the area to be treated to promote growth of new hair where no hair is growing or to retard the loss of hair;

allowing said layer to be undisturbed on said body surface for at least about 25 to about 40 minutes; and rinsing said layer from said surface area with clean water uncombined with any cleaning agent.

7. The method of claim 6 wherein the steps are repeated for a period of at least about 15 days.

8. The method of claim 6 wherein the steps are repeated for a period of at least about 60 days.

9. A method for the restoration of hair growth or for the retardation of hair loss which comprises topically applying to the human scalp an effective amount of Dead Sea mud.

10. The method of claim 9 wherein said Dead Sea mud is washed and filtered prior to applying it to the scalp.

11. The method of claim 10 wherein said Dead Sea mud is washed and filtered to remove gravel and sand.

12. The method of claim 11 wherein said Dead Sea mud is subjected to mechanical mixing.

13. The method of claim 12 wherein a scent producing agent is mechanically mixed into said Dead Sea mud.

14. The method of claim 12 wherein at least one anti-bacterial agent is mechanically mixed into said Dead Sea mud.

15. The method of claim 12 wherein a phase stabilizer is mechanically mixed into said Dead Sea mud.

16. The method of claim 12 wherein an inert filler is mechanically mixed into said Dead Sea mud.

17. The method of claim 12 wherein a scent producing agent and at least one anti-bacterial agent are mechanically mixed with said Dead Sea mud.

18. The method of claim 17 wherein a phase stabilizer is mechanically mixed with said Dead Sea mud.

19. The method of claim 17 wherein an inert filler is mechanically mixed with said Dead Sea mud.

* * * * *